United States Patent [19]

Hershberg et al.

[11] 4,070,356
[45] Jan. 24, 1978

[54] MANUFACTURE OF SOLUBLE SULFATHIAZOLE

[75] Inventors: Emanuel B. Hershberg, West Orange; James E. Christensen, Westfield, both of N.J.

[73] Assignee: MBH Chemical Corporation, Orange, N.J.

[21] Appl. No.: 651,293

[22] Filed: Jan. 22, 1976

[51] Int. Cl.$^2$ .............. C07D 275/00; C07D 277/00; C07D 285/00; A01N 9/22
[52] U.S. Cl. ................. 260/239.95; 424/229
[58] Field of Search ............. 260/239.95, 306.8; 424/270

[56] References Cited

U.S. PATENT DOCUMENTS

| | | | |
|---|---|---|---|
| 2,330,223 | 9/1943 | Kyrides | 260/306.8 R |
| 2,339,083 | 1/1944 | Leitch et al. | 260/239.95 |
| 2,392,125 | 1/1946 | Dhein | 260/239.95 |
| 2,396,711 | 3/1946 | Lott | 260/239.95 |

*Primary Examiner*—Albert T. Meyers
*Assistant Examiner*—D. W. Robinson
*Attorney, Agent, or Firm*—Ostrolenk, Faber, Gerb & Soffen

[57] ABSTRACT

A method is disclosed for overcoming production problems associated with the commercial manufacture of sodium sulfathiazole in soluble form involving the formation of hydrates under controlled conditions wherein the water content is maintained in the range of about 4.5 to 6 mols of water to each mol of sodium sulfathiazole, equivalent to a water content of from about 23 to 28% by weight of the resulting hydrate and said hydrate is kept in a molten state at an optimum temperature of from about 53 to 59° C.

9 Claims, No Drawings

MANUFACTURE OF SOLUBLE SULFATHIAZOLE

BACKGROUND OF THE INVENTION

Sulfathiazole (N-2-thiazolysulfanilamide) is a highly useful product, particularly in therapeutic applications. It is a valuable antimicrobical sulfa drug and it is widely used in veterinary medicine. It is most often administered by addition to the drinking water or liquid feed of animals. For example, it is used in the drinking water for treatment of diseases of swine and poultry, and in fish tanks for treatment of tropical fish. In order to be so administered, it must be prepared in a water soluble form. Most commonly, it is administered as the water soluble sodium salt.

Sodium sulfathiazole forms a hydrate which is a solid or substantially solid solution with water. The hydrates range from the monohydrate up through and including the decahydrate. As the water content is increased, the melting point is correspondingly decreased.

Two hydrates are of particular importance in veterinary medicine. They are the pentahydrate and the sesquihydrate. The pentahydrate is specified in the British Veterinary Codex, and the sesquihydrate is the most commonly used soluble form in proprietary sulfa combinations in the United States for animal husbandry and is described in the National Formulary X.

In the preparation of the soluble form of sulfathiazole, i.e. the sodium derivative, certain problems have been encountered. In order to understand the obstacles facing the separation of soluble sodium sulfathiazole, it is helpful to review the procedure heretofore employed for its manufacture. That procedure conventionally involves dissolving sulfathiazole in a warm aqueous sodium hydroxide solution. Thereafter, the solution is cooled and filtered. The filtrate, or mother liquor, contains about ten to twenty percent of the sodium sulfathiazole. The mother liquor must be processed further in order to recover its sulfathiazole. It can be concentrated by evaporation or drying or by other conventional means so that repeated filtration will permit recovery of the sulfathiazole.

The crystalline solid collected on the filter is spread out on trays to be dried in a forced convection air drying oven or in a fluid-bed dryer. Samples are frequently taken and analyzed for their water content and depending upon the end use desired, the drying process is interrupted when the appropriate hydrate stage, e.g. the pentahydrate or sesquihydrate, is reached.

At the point at which the sulfathiazole is dissolved in the aqueous sodium hydroxide solution, problems are encountered unless the water content is maintained to a relatively large excess, i.e. at least to the equivalent of the heptahydrate. If less water is used, the solid which crystallizes is difficult to stir and solidifies to a hard cake. However, the use of such a large excess of water serves to lower the melting point such that partial melting occurs during the drying stage and that remains true even at moderate temperatures in the fluid-bed dryer, or the forced convection air drying oven. The result is that the product is not uniform and requires further processing. Moreover, it should be noted that removal of water is costly, hence an excess of water makes the process that much more uneconomical and commercially undesirable.

Another problem encountered is degradation and darkening of the product upon prolonged exposure to high concentrations of alkali at elevated temperatures. Thus, it is desirable to employ a moderate temperature and simultaneously accomplish drying within a reasonable amount of time so that the time of exposure to the alkali is minimized. An excess of water would reduce the concentration of alkali, but as noted earlier, an excess serves only to reduce the melting point and present further problems. Simply employing a lower temperature does not of itself solve the problem of degradation because lowering the temperature serves only to increase the time of drying and thus increases the exposure of the product to the alkali in the solution. Decreasing the water content which favors accelerated drying at a more moderate temperature serves, however, to increase the concentration of alkali in the solution and also presents the crystallization problem noted earlier. It also brings the melt too close to its solidification point.

OBJECT OF THE INVENTION

Hence, it is an object of this invention to be able to form a soluble sulfathiazole in a reasonably economical and commercially useful manner so that the sulfathiazole product may maintain its valuable therapeutic applications, and yet overcome the problems associated with its manufacture in a soluble form.

It is a further object of this invention to permit complete recovery of the sulfathiazole in a single process step thereby eliminating the need to reprocess the initial sodium sulfathiazole solution.

It is also an object of this invention to provide a means for the manufacture of sodium sulfathiazole without subjecting the product to degradation.

Other objects, features and advantages of the invention will become apparent to those skilled in the art from the following description.

SUMMARY OF THE INVENTION

The present invention provides a novel process for the manufacture of sulfathiazole in soluble form. It has been discovered that the addition of sulfathiazole to an aqueous sodium hydroxide solution so that water is present at a ratio of from about 4.5 to about 6 molecules of water for each molecule of sodium sulfathiazole will give rise to a molten fluid. The aforesaid ratio of water to sulfathiazole corresponds to a range of from about 23 to about 28 percent water content in the resulting hydrate.

By maintaining the temperature of that molten fluid within the broad range of about 50° to about 63° C. and preferably about 53° to 59° C. and thereafter cooling the vessel or pouring the filtrate into suitable containers for solidification, the resulting solid is highly crystalline and may be fractured along crystal planes and transversely in a manner which permits rapid and easy milling to a powder. No dust is formed. The powder may then be dried in the conventional manner without fear of degradation.

It will be observed that the molten fluid need not be filtered prior to freezing and there is no loss or waste involved. The fluid can, of course, be filtered but the purpose of such filtration is to remove any particulate matter, e.g. dirt particles. The filtrate contains one hundred percent of the sulfathiazole. Hence, there is no need for reprocessing as with conventional methods.

DESCRIPTION OF PREFERRED EMBODIMENTS

In the practice of this invention, after sulfathiazole is added to aqueous sodium hydroxide, a sample of the resulting melt of molten fluid is withdrawn and permitted to crystallize. That portion of crystalline material is then dissolved in water to make a ten percent aqueous solution whose pH must then fall within the limits of from about 9 to about 11, and preferably from about 9.5 to about 10.5. The above adjustment is conventional and is made here to correct the ratio of sulfathiazole to alkali which is otherwise approximately present in a 1:1 molecular ratio.

The amount of water required is obtained by adding about 4 mols of water for each mol of sulfathiazole. It should be observed that one additional mol of water is derived from the neutralization process.

The temperature range in which the molten fluid is to be maintained is broadly from about 50° C. to about 63° C. and preferably about 53° C. to about 59° C.

The molten fluid should be held for as short a time as possible at that temperature prior to its crystallization.

The molten fluid may be filtered, for example, after decolorization with charcoal, but it should be observed that filtration is an optional step designed to remove dirt particles. Since the sulfathiazole is a liquid at these temperatures, it will pass through the filter.

Thereafter, the molten fluid is cooled below about 50° C. preferably to about ambient temperature. It will be observed that when the temperature drops below the melting point of the fluid, it turns into a crystalline solid.

The resulting solid may then be ground to any desired size, for example, to a fineness of 16 mesh. The objective of grinding is simply to make a rapidly dissolving material.

The crystalline cake has the property of fracturing without creating dust.

The resulting product is water-soluble and has a water content in the range of from about 23 to about 28 percent by weight. Optimally, the pentahydrate will have a water content of 24.5 percent.

The following examples describe in detail the preparation of soluble sulfathiazoles according to this invention:

EXAMPLE 1

250 kg. of sulfathiazole is added to a caustic soda solution derived from 40 kg. of caustic soda and 83 kg. of water. The resulting clear solution is maintained at a temperature of 53° – 59° C., filtered to remove particulate matter and cast into trays approximately 12 cm. deep with sloping sides to permit easy cake removal. The contents of the trays solidify upon standing overnight at ambient temperatures and the cake is removed by inverting the trays.

The cakes are broken into large lumps with a mallet and then ground in a hammer mill to a fineness of about 60 mesh. It is then dried to the sesquihydrate range of water content in a forced-draft convection oven. The product shows no sign of degradation.

EXAMPLE 2

250 kg. of sulfathiazole is added to a caustic soda solution derived from 40 kg. of caustic soda and 83 kg. of water. The resulting clear solution is maintained at a temperature of 53° – 59° C., filtered to remove particulate matter and cast into trays approximately 12 cm. deep with sloping sides to permit easy cake removal. The contents of the trays will solidify upon standing overnight at ambient temperatures and the cake removed by inverting the trays.

The cakes are broken into large lumps with a mallet and then ground in a hammer mill to a fineness of 60 mesh or larger. It is then dried to the pentahydrate range of water content in a fluid bed dryer. The product shows no sign of degradation.

The yield is quantitative, (360 kg.), the only losses being the mechanical losses incurred in the transfer, grinding and drying operations.

EXAMPLE 3

250 kg. of sulfathiazole was dissolved at 55° C. in a previously prepared solution from 40 kg. of caustic soda and 180 kg. of water to form a complete solution. Upon cooling, a crystalline solid separates which was centrifuged from the mother liquor. 315 kg. of pentahydrate (87% theory) was obtained. Further product may be obtained by concentrating and reprocessing the mother liquor.

Various changes and modifications can be made in the process of the instant invention without departing from the spirit and scope thereof. The various embodiments described herein were for the purpose of illustrating the invention but were not intended to limit it.

What is claimed is:

1. In the production of hydrates of sodium sulfathiazole, by contacting sulfathiazole with aqueous NaOH in approximately equimolar amount and recovering the resulting hydrate, the improvement which comprises adjusting the water content of the aqueous sodium hydroxide sulfathiazole solution such that the mol ratio of water to sodium sulfathiazole is about 4.5 to 6, and maintaining the temperature at a range of about 50° to 63° C. until a clear solution is formed, and the molten hydrate is then poured into containers and allowed to cool and solidify.

2. A method as defined in claim 1 wherein said temperature is about 53° – 59° C.

3. A method as defined in claim 1 wherein the solution is filtered to remove particulate matter.

4. A method as defined in claim 1 wherein after formation of the solution, the temperature is lowered to solidify said hydrate.

5. A method as defined in claim 4 wherein the solid is milled into powder form.

6. A method as defined in claim 4 wherein the temperature is lowered to ambient temperature.

7. A process for the preparation of sodium sulfathiazole in soluble form suitable for administration to animals in their drinking water or feed which comprises dissolving sulfathiazole in an aqueous sodium hydroxide solution in approximately equimolar amount, wherein the water content is such that there are about 4.5 to 6.0 mols of water for each mol of sulfathiazole corresponding to a water content of about 23 to 28 percent by weight of the sodium sulfathiazole hydrate thus formed, maintaining the temperature of the aqueous sodium sulfathiazole solution at a range of about 53° to 59° C. until a clear solution is formed, wherein the sodium sulfathiazole is maintained in a fluid molten state, casting said fluid into molds, and cooling, whereby said sodium sulfathiazole fluid is transformed into a highly crystalline solid cake, converting said cake into powder form, and drying said powder.

8. The process of claim 7 wherein the fluid sodium sulfathiazole is filtered to remove particulate matter prior to casting in molds.

9. The process of claim 7 wherein the fluid sodium sulfathiazole is decolorized with charcoal prior to filtration.

* * * * *